United States Patent
Moltani et al.

(10) Patent No.: US 10,736,568 B2
(45) Date of Patent: Aug. 11, 2020

(54) SENSOR FOR MEASUREMENT OF PHYSIOLOGICAL ELECTRICAL SIGNALS

(71) Applicant: COMFTECH S.R.L., Monza (IT)

(72) Inventors: Lara Alessia Laura Moltani, Monza (IT); Giuseppe Andreoni, Muggio (IT)

(73) Assignee: COMFTECH S.R.L., Monza (IT)

( * ) Notice: Subject to any disclaimer, the term of this patent is extended or adjusted under 35 U.S.C. 154(b) by 531 days.

(21) Appl. No.: 15/326,297

(22) PCT Filed: Jul. 15, 2014

(86) PCT No.: PCT/IB2014/063109
§ 371 (c)(1),
(2) Date: Jan. 13, 2017

(87) PCT Pub. No.: WO2016/009251
PCT Pub. Date: Jan. 21, 2016

(65) Prior Publication Data
US 2017/0196514 A1  Jul. 13, 2017

(51) Int. Cl.
*A61B 5/00* (2006.01)
*A61B 5/0408* (2006.01)

(52) U.S. Cl.
CPC ........ *A61B 5/6804* (2013.01); *A61B 5/04085* (2013.01); *A61B 5/68* (2013.01);
(Continued)

(58) Field of Classification Search
CPC ..... A61B 5/04085; A61B 5/68; A61B 5/6801; A61B 5/6802; A61B 5/6804;
(Continued)

(56) References Cited

U.S. PATENT DOCUMENTS

| 2006/0094948 A1 | 5/2006 | Gough et al. |
| 2006/0211934 A1 | 9/2006 | Hassonjee et al. |

(Continued)

FOREIGN PATENT DOCUMENTS

| EP | 1925718 A2 | 5/2008 |
| EP | 2671506 A1 | 12/2013 |

(Continued)

OTHER PUBLICATIONS

Song, H.Y., et al., "Textile Electrodes of Jacquard Woven Fabrics for Biosignal Measurement", Journal of the Textile Institute, vol. 101, No. 8, Aug. 1, 2010, pp. 758-770.

(Continued)

*Primary Examiner* — Ronald Hupczey, Jr.
(74) *Attorney, Agent, or Firm* — Pearne & Gordon LLP

(57) ABSTRACT

A sensor for measuring physiological electric signals, including: a textile electrode including a detecting portion having an electrically conductive detecting surface area; a peripheral textile portion; a first electrical connection electrically connected to an acquisition and processing device, and an electrical connection that electrically connects the textile electrode to the electrical connector, the electrode having a three-dimensional textile structure made by interweaving warp threads and weft threads, the detecting portion including an upper textile layer and a lower textile layer, arranged below the upper layer and joined to the latter along a perimeter joining line so as to create a cavity defined by the joining line and to define a region outside the joining line that includes the peripheral textile portion, the cavity being filled by a filler material so that the detecting textile portion protrudes in height with respect to the peripheral textile portion.

20 Claims, 5 Drawing Sheets

(52) U.S. Cl.
CPC ........... *A61B 5/6802* (2013.01); *A61B 5/6823* (2013.01); *A61B 2562/043* (2013.01); *A61B 2562/125* (2013.01)

(58) Field of Classification Search
CPC . A61B 5/6813; A61B 5/6823; A61B 2562/04; A61B 2562/043; A61B 2562/125
See application file for complete search history.

(56) References Cited

U.S. PATENT DOCUMENTS

| | | |
|---|---|---|
| 2007/0127187 A1 | 6/2007 | DeFusco et al. |
| 2008/0045808 A1 | 2/2008 | Hassonjee et al. |
| 2009/0112079 A1 | 4/2009 | Hassonjee et al. |
| 2009/0203984 A1 | 8/2009 | Dias et al. |
| 2009/0227856 A1* | 9/2009 | Russell .............. A41D 13/1281 600/388 |
| 2011/0288394 A1 | 11/2011 | Hassonjee et al. |
| 2012/0265025 A1* | 10/2012 | Hsiao ....................... A61B 5/04 600/300 |
| 2014/0135608 A1 | 5/2014 | Gazzioni et al. |

FOREIGN PATENT DOCUMENTS

| | | |
|---|---|---|
| EP | 2676603 A1 | 12/2013 |
| WO | 2006060934 A1 | 6/2006 |
| WO | 2009043196 A1 | 4/2009 |
| WO | 2012140522 A2 | 10/2012 |

OTHER PUBLICATIONS

Catarino, A., et al., "Continuous health monitoring using E-textile integrated biosensors", The Proceedings of International Conference and Exposition on Electrical and Power Engineering (EPE), Oct. 25-27, 2012, Iasi, Romania, pp. 605-609.

* cited by examiner

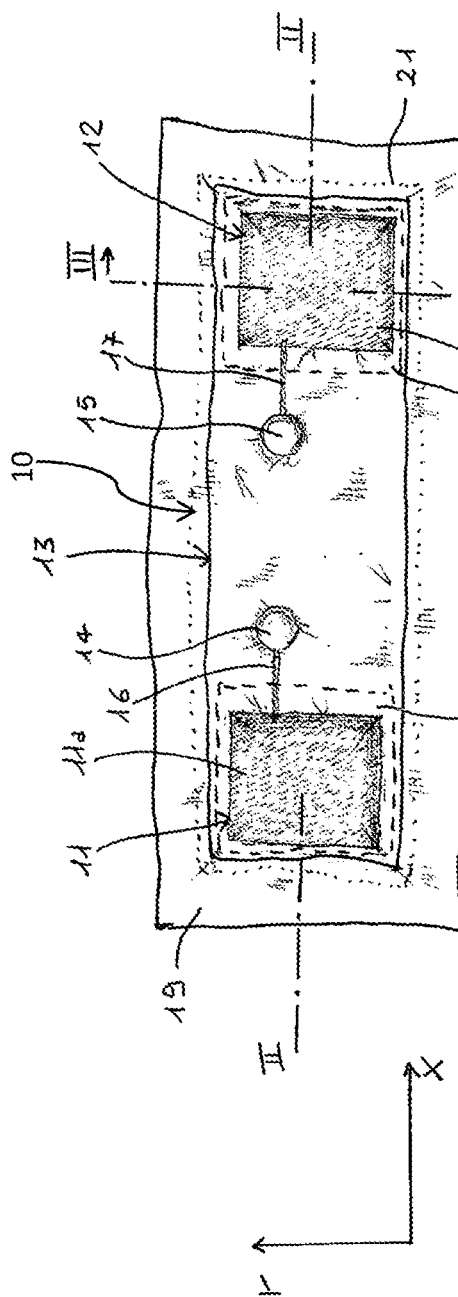
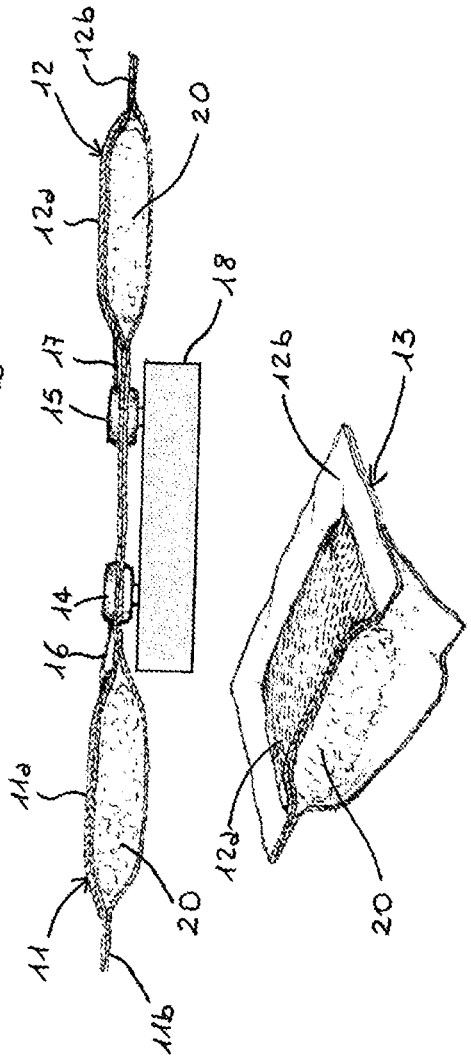

SENSOR FOR MEASUREMENT OF PHYSIOLOGICAL ELECTRICAL SIGNALS

FIELD OF THE INVENTION

The present invention relates to a sensor for measuring physiological electric signals.

STATE OF THE ART

The biomedical and/or biometric electric signals, or in short biosignals, most frequently measured are electrophysiological signals, such as ECG (electrocardiogram), EEG (electroencephalogram), EMG (electromyography), EDA (electro-dermal activity) or also called GSR (galvanic skin response), the movement of the body or of some of its anatomical regions and respiratory activity. Recently, biomedical sensors have been developed, i.e. for measuring electrophysiological signals, that can be worn for measuring and/or monitoring patients at home, in hospital, in daily life or by athletes during physical-sports activities. Sensors having one or more electrodes based on is conductive textile fibres have various advantages, including being flexible, comfortable and easy to integrate in a garment.

Conductive fibres interwoven or knitted in textile structures produce textile electrodes that, when they are connected to a measurement system, allow the measurement and/or monitoring of electrical potentials.

Patent application EP 2676603 concerns a sensor-enabled label made from fabric for detecting and transmitting electrical signals or vital parameters of a user, comprising a fabric obtained from yarns, a layer of conductive fabric integrated in said fabric obtained from yarns defining a plurality of electrical signal transducers, at least one electrical connector for the connection to a processing device, in which the electrical connector is in signal communication with the layer of conductive fabric through an electrical connection. The sensor-enabled label comprises an impedance adapter configured so as to adapt the impedance value existing between the plurality of transducers and the skin of the user, when the sensor-enabled label is placed in contact with the skin of the user.

Patent application US 2006/0094948 concerns an electrode device that comprises an electrically conductive electrode portion having a mesh-style construction, sewn or glued on a textile article. A portion of material that is impermeable to the conduction of humidity and electrically conductive is attached to the electrode portion, the two portions being placed in contact with the skin of a user. The portion that is impermeable to humidity promotes the collection of perspiration between the skin and the portion of material and in this way it restricts the area in which the skin is able to perspire. The presence of humidity or perspiration decreases the electrical resistance between the skin and the portion of material.

Patent application EP 2671506 describes a three-dimensional textile electrode with a tubular structure of weft knitting fabric. The electrode is produced using conductive threads, based on silver or conductive polymers, together with elastomeric threads, like elastam. The application states that the described solution makes it possible to maintain the contact between electrode and skin and the correct positioning is ensured by the compression promoted by the three-dimensional structure and by the combination of threads that constitute the electrode. In order to increase the thickness of the electrode, a support element, of foam or silicone, can be inserted after the production of the tubular structure through the opening of the tube.

Publication WO 2012/140522 concerns a device that comprises a substrate and a textile electrode arranged on the substrate and at least one first conductive element, in which the electrode comprises a plurality of textile fibres a certain number of which are made from electrically conductive material, arranged in a substantially vertical direction at the upper surface of the substrate. A second plurality of fibres are made from super-absorbent material that makes it possible to maintain the contact with the humidity of the skin and thus the contact between skin and electrode.

Application WO 2006/060934 describes a textile device for electrophysiological or electrostimulation measurements that comprises a textile layer that is placed in contact with the surface of the body of an individual wearing the device. The side that makes contact with the skin is equipped with a group of electrodes, at least one of which has a height of at least 1 mm and is embroidered on the textile layer.

A study on the monitoring of the disabled and the elderly that uses integrated textile electrodes for ECG measurements is described by A. Catarino et al. in "Continuous health monitoring using E-textile integrated biosensors", published in the proceedings of International Conference and Exposition on Electrical and Power Engineering (EPE), 25-27 Oct. 2012, Iasi, Romania, page 605. The solution proposed by the authors is based on weft knitting technology. The frame used is a machine for stitchless knitted fabrics, which is also a jacquard machine, with which it is possible to obtain complex structures with local variations. The authors write that such a characteristic was used to produce particularly voluminous structures at the area used as electrode. In this way, the electrode protrudes from the rest of the fabric, improving the contact between skin and electrode. The same knitting technology has allowed the integration of electrical connection in the textile substrate.

The woven fabric, being an interwoven fabric in which, generally, the weft thread passes over and under each warp thread, can be made with more uniform characteristics than a knitted fabric and has a low tendency to stretch. H.-Y Song et al. in "Textile electrodes of jacquard woven fabrics for biosignal measurement", published in The Journal of The Textile Institute, vol. 101 (2010), pages 758-770 describes textile electrodes for physiological monitoring with the conductive thread in a double layer jacquard fabric structure consisting of a bottom layer of polyester thread and an effective layer of thread coated with silver woven in the direction of the weft. The article studied two groups of textile electrodes, the first group with 100% of warp ends not removed from the fabric and the second group with 50% of warp ends removed, in which the electrode was convex or flat, with or without conductive paste between the snap connector and the textile electrode. The authors concluded that the convex shape was better than the flat shape because the convex electrode was in closer contact with the skin and that the conductive paste reduced the contact resistance and improved the quality of the signal.

SUMMARY OF THE INVENTION

According to preferred embodiments the present invention relates to a sensor for measuring physiological electric signals, comprising:

a first textile electrode that comprises a detecting textile portion for detecting physiological electric signals and a peripheral textile portion directly adjacent to the detecting portion, in which the detecting surface area is intended to come into contact with the skin of an individual and is electrically conductive, and a first electrical connection configured to electrically connect the first textile electrode to a first electrical connector, in which the first textile electrode has a three-dimensional textile structure made by weaving together warp threads and weft threads, in which the detecting portion comprises an upper textile layer the upper surface of which extends over the detecting surface area and a lower textile layer, arranged below the upper layer and joined to it along a perimeter joining line so as to create a cavity defined by the joining line and define a region outside of the joining line that comprises the peripheral textile portion, and the cavity is filled by a filler material so that the detecting textile portion protrudes in height with respect to the peripheral textile portion.

The sensor preferably comprises the first electrical connector electrically connected to an acquisition and processing device of the physiological signals detected by the first textile electrode.

In an embodiment, the upper surface of the upper textile layer substantially corresponds to the detecting surface area.

In some embodiments, the textile structure of the first electrode is a double fabric, in which the detecting portion is formed from two separate textile layers corresponding to the upper layer and to the lower layer, respectively, and the peripheral portion is interwoven in a single layer.

At least one conductive thread is arranged in the warp and/or in the weft of the upper textile layer of the detecting portion.

Preferably, the peripheral textile portion comprises a non-electrically conductive peripheral surface area, arranged adjacent to and in contact with (i.e. directly adjacent to) the detecting surface area. The non-electrically conductive peripheral surface area preferably extends externally from the perimeter joining line.

In some embodiments, the warp threads and/or the weft threads are elastic, preferably comprising an elastomeric polymer fibre.

Preferably, the conductive thread is an elastomeric polymer fibre coated in metal.

Preferably, the textile structure of the first electrode is a double warp Jacquard fabric, in which the detecting portion is an open warps fabric made up of the upper textile layer and the lower textile layer, separate from one another, and the peripheral textile portion is a closed warps fabric interwoven in a single layer.

Preferably, the textile electrode is manufactured in Jacquard fabric in a single piece.

In some embodiments, the first textile electrode is made from fabric by weaving electrically conductive threads with functional threads so that conductive threads are arranged on the surface area of the detecting portion exposed for contact with the skin of whoever wears the sensor, while the conductive threads remain enclosed inside the fabric at a non-electrically conductive peripheral surface area comprised in the peripheral portion and directly adjacent to the detecting surface area, and in which the functional threads are exposed on the peripheral surface area, while the conductive threads remain enclosed inside the fabric at the same peripheral surface area.

In an embodiment, the functional threads and/or the conductive threads are elastic threads comprising an elastomeric polymer fibre.

Preferably, the peripheral portion of the textile electrode comprises a textile Connection region having a connection surface area adjacent to and outside the non-electrically conductive peripheral surface area, the conductive threads being exposed on the connection surface area, the first electrical connection being made from conductive threads enclosed inside the fabric of the peripheral portion and that extend from the detecting surface area to the connection region. In the preferred embodiments, a first electrical connector is arranged in contact with the connection region for the connection with an acquisition and processing device of the signals detected by the textile electrode. In some embodiments, the connection surface area is directly adjacent to the non-electrically conductive peripheral surface area.

In some embodiments, the sensor comprises a textile sensor structure woven into a single piece by interweaving electrically conductive threads with functional threads, in which the textile structure of the first electrode is integrated, the textile sensor structure comprising a second textile electrode arranged outside the peripheral portion of the first textile electrode and a second electrical connection configured to electrically connect the second textile electrode with a second electrical connector. In an embodiment, a second connector is foreseen electrically connected to the second textile electrode through the second connection, in which the first and the second connector are electrically connected to an acquisition and processing device of the signals detected by the first and by the second electrode. Preferably, the second textile electrode comprises a detecting textile portion having a detecting surface area for detecting physiological electric signals and a peripheral textile portion directly adjacent to the detecting portion, in which the detecting surface area is intended to come into contact with the skin of an individual and is electrically conductive. Preferably, the second textile electrode has a three-dimensional textile structure made by interweaving warp threads and weft threads, in which the detecting portion comprises an upper textile layer the upper surface of which extends over the detecting surface area and a lower textile layer, arranged below the upper layer and joined to the latter along a perimeter joining line so as to create a cavity defined by the joining line and to define a region outside the joining line comprising the peripheral textile portion, and the cavity is filled by a filler material so that the detecting textile portion protrudes in height with respect to the peripheral textile portion.

Preferably, the filler material of the cavity of the first textile electrode (and preferably of the second textile electrode) is a polymeric fibre. Preferably, the filler material is hydrophilic. In some preferred embodiments, the filler material is a hydrophilic ball of polymeric fibre, preferably a continuous fibre of microfiber polyester.

In some preferred embodiments, the electrically connection is an electrically conductive and elastic textile string. Preferably, the textile string is a bundle of woven textile fibres that comprises electrically conductive threads, in which the conductive threads are elastic and/or the bundle also comprises elastic functional threads. In an embodiment, the textile string is a bundle of interwoven textile fibres of elastomeric polymer coated with a metallic coating.

In some embodiments, the peripheral textile portion protrudes outwards by a variable height comprising at least one recess.

In some embodiments, the textile structure of the first electrode is a double fabric, in which the detecting portion is formed from two separate textile layers corresponding to the upper layer and to the lower layer, respectively, and the peripheral portion is woven into a single layer, and in which the detecting surface area comprises a recess so that the detecting portion protrudes outwards by a variable height, the recess being formed by joining the upper layer to the lower layer by weaving at a point inside the detecting surface area.

Preferably, the detecting surface area comprises a plurality of recesses.

Preferably, the recess or the plurality of recesses are formed in the double fabric of the textile electrode structure through a single weaving process. In an embodiment, a surface and complex 3D morphology (alternation of concavity and convexity, even multiple) of the detecting portion with variable thickness can be obtained by setting the textile structure during the production step.

A protrusion in height outwards made through the insertion of a filler material makes it possible to create protrusions of variable size for a specific application, for example depending on the amount of polymeric fibre inserted in the cavity and thus on the size of the fibre ball.

In some embodiments, the protrusion height of the detecting portions is comprised between 0.1 mm and 10 mm.

The biomedical and/or biometric sensor according to the present invention can be integrated in a garment that once worn places one or more electrodes in contact with the skin or applied directly to the skin of a user.

In some embodiments, the present invention relates to an article able to be worn to monitor the physiological electric signals of a person wearing such an article, comprising a sensor according to the present disclosure, in which:

the sensor comprises a textile sensor structure that comprises the textile structure of the electrode, the textile sensor structure having an outer edge that is peripheral with respect to the textile electrode, the sensor is fixed to the garment with the detecting surface area facing outwards through a band that at least partially surrounds the textile sensor structure and that lays over the outer edge of the textile sensor structure and over a portion of the article directly adjacent to the textile structure so as to fix the textile structure onto the article, and the band is made from polymeric material that is impermeable to water and not breathable.

The presence of a band that is impermeable to water and not breathable as lateral and/or upper/lower coating (i.e. skin side or outer side) with respect to the electrode increases local sweating improving the conductive properties of the sensor/electrode-skin contact. Through the application of a polymeric band that is impermeable to water and not breathable in a region adjacent to the detecting portion of the sensor the local increase in sweating and perspiration is promoted, as well as the impermeabilization from external agents, and the presence of sliding between textile electrode and skin during measurement and monitoring, which can lead to artefacts in the signal acquired, is reduced.

Preferably, the band entirely surrounds the textile sensor structure.

In some embodiments, the configuration of the electrode, with the conductive portion protruding with respect to the main surface of the textile electrode, together with the presence of a band made from impermeable and non-breathable material in a region close to the active region of the sensor, increases the adhesion of the electrode to the skin and at the same time the local humidity at the electrode-skin interface, thus further improving the efficiency of the detection of biosignals.

Preferably, the band is made from elastomeric polymeric material, more preferably having elongation at break greater than or equal to 150%.

In an embodiment, the band is made from biocompatible polyurethane.

Preferably, the band is applied through thermal bonding to glue the sensor to the article, more preferably thermo-bonded.

The band has a free upper surface, arranged on the side of the detecting surface area. Preferably, the detecting portion protrudes in height outwards with respect to the upper surface of the band.

In some embodiments, the lower textile layer of the detecting portion is made from electrically conductive fabric.

In some preferred embodiments, the first electrical connector and, if present, the second electrical connector, is a press-button of metallic material.

BRIEF DESCRIPTION OF THE FIGURES

The characteristics and advantages of the present invention will become clearer from the following detailed description of some preferred embodiments, illustrated as a non-limiting example in the attached figures, which should be considered as schematic representations not to scale, in which:

FIG. 1 is a perspective view from above of a biomedical and/or biometric sensor according to an embodiment of the present invention.

FIG. 2 is a cross section of the biomedical and/or biometric sensor of FIG. 1, along the line II-II indicated in FIG. 1.

FIG. 3 is a perspective section view of the sensor of FIG. 1 along the line III-III.

DETAILED DESCRIPTION OF THE PREFERRED EMBODIMENTS OF THE INVENTION

Figure 4:
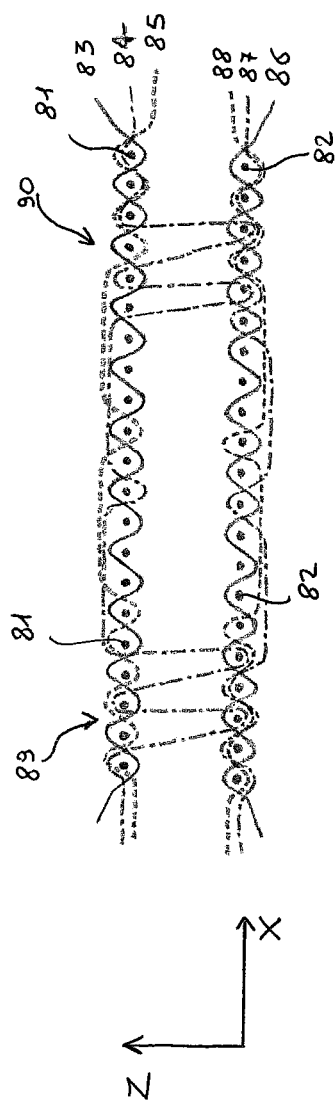
FIG. 4 schematically shows an example architecture of a 3D structure of Jacquard fabric.

FIG. 1 schematically shows a view from above of a sensor for measuring physiological electric signals according to an embodiment of the present invention. FIG. 2 is a cross section of the sensor of FIG. 1, along the line II-II, indicated with a dotted and dashed line in FIG. 1 (the element 19 shown in FIG. 1 has been left out in FIGS. 2 and 3). A biomedical and/or biometric sensor 10 comprises a textile structure 13 that has a free upper surface that is intended to come into contact with the body, i.e. with the skin, of an individual who wears the sensor during its use and an opposite rear surface (not visible in FIG. 1). The upper surface of the textile structure 13 extends mainly in a reference plane XY. The textile structure comprises a first textile electrode 11 and a second textile electrode 12, separated from one another by a distance along the direction X of the plane XY. In the present embodiment, as described in greater detail hereafter, the first and the second electrode are formed in the textile structure 13. In the embodiment of FIGS. 1-3, the structure 13 is rectangular in shape, however it should be understood that the geometric shape of the textile structure is purely an example.

Each electrode 11, 12 comprises a respective detecting portion 11a and 12a, suitable for detecting the physiological electric signals coming from the individual wearing the sensor and that protrudes with respect to a respective peripheral fabric portion 11b and 12b, arranged adjacent to the detecting portion of each electrode and that lies on the reference plane XY. The textile region 11b and 12b corresponding to the peripheral portion is indicated in FIG. 1 with the area, which surrounds the respective detecting portion, defined by a broken line. The peripheral portion is adjacent to and in contact with the respective detecting portion.

The detecting portion 11a and 12a has an electrically conductive fabric upper surface, which is intended to come into contact with the skin of an individual wearing the sensor and thus create an electrode-skin electrical contact. In particular, the detecting portion extends over an electrically conductive surface area.

The biomedical and/or biometric sensor of the present embodiment can be used to measure ECG (electrocardiogram) signals, by measuring the potential difference between the two electrodes 11 and 12 when they are both placed on the body surface.

In the present embodiment, the respective peripheral portions to the portions 11a and 12a are comprised in the portion of the textile structure 13 different from the detecting portions 11a and 12a of the electrodes 11 and 12. Preferably, the upper surface of each peripheral portion 11b and 12b is made from non-electrically conductive fabric, and therefore it is not suitable for detecting physiological electric signals. Preferably, the peripheral portion of each electrode directly surrounds the detecting portion thereof.

Each detecting portion of electrically conductive fabric is woven with electrically conductive threads or fibres. In the preferred embodiments, the electrically conductive fabric is formed from at least one conductive thread, suitable for transporting electric current, woven with at least one functional thread, not electrically conductive and having a support and/or structural function. In some embodiments, the at least one conductive thread is arranged in one of the two warp or weft directions, while the at least one functional thread is arranged in the other of the two warp or weft directions and crosses over the at least one conductive thread. The interweaving of weft threads with the warp threads is created through a frame. In other embodiments, the conductive fabric is made with conductive thread both in weft and in warp. The threads with conductive properties can be metallic threads, for example thin silver threads, or metallized fibres, generally fibres of polymeric material coated with a metallic coating so as to form an electrically conductive surface. Preferably, the conductive threads are metallized fibres that can be interwoven or knitted in fabrics, for example polyamide fibres coated with silver. In some preferred embodiments, the conductive threads are polymeric monofilaments coated in metal. The polymeric material of the fibre can be a synthetic polymeric material such as polyester or polyamide, for example nylon.

In some embodiments, the conductive threads that make up or are comprised in the electrode can be formed from a composite material with synthetic and natural components, i.e. consisting of a synthetic polymeric material mixed with one or more natural fibres, such as cotton or wool. In some embodiments, the conductive threads can be formed from a conductive thread interwoven with elastam to obtain an elasticized thread or they can be elastam threads coated in metal. The choice of the polymeric material that constitutes the fibre is made in accordance with the physical and/or chemical characteristics desired, for example elongation at break under traction, flexibility, weight, production technology most suitable for the garment that incorporates or on which the sensor is fixed (e.g. seamless, cut and sewn, knitted) and the anatomical-anthropometric positioning of the sensors on the body of the individual wearing them, whether or not they are integrated in a garment.

Typically, silver is preferred as coating metal due to the good contact with the skin, its anti-bacterial properties and the possibility of forming a very thin and adherent coating, which does not modify the physical properties of the polymeric fibre, such as elongation at break.

Each electrode is connected to a respective electrical connector 14 and 15, for example but not for limiting purposes, a connector of the type known as "snap-on connector" or metallic press-button, both in the crown versions and in the bayonet versions through a respective electrical connection 16, 17. Such an electrical connection 16, 17 can be a metallic thread or a textile thread formed from a polymeric fibre coated with electrically conductive material like, for example, silver, steel, or carbon copper. In some embodiments, the electrical connection from the detecting portion to the connector is made with a textile string of woven conductive threads. The bundle of threads can be woven, in known ways, with a braiding machine in the form of a braid, strip, coil, cord or with a tubular profile. The electrical connection cans be either elastic or rigid in elongation, flexing and/or twisting, the resulting mechanical property depending on the processing of the threads of which it consists and/or on the material from which the threads are made. In some embodiments, the textile string is a bundle made up of conductive threads woven with functional threads having a high elastic elongation at break. In other embodiments, the textile string is a bundle of conductive threads made up of fibres of polymeric material having high elastic elongation at break coated with a conductive layer. In an embodiment, the textile string is a bundle of elastam threads woven and coated with a silver coating. In a different embodiment, the string is a group of silver threads woven with elastam threads.

Since many applications can require a finite and non-negligible length of the electrical connection from the electrode to the connector, an electrical connection under elastic deformation makes it possible to follow the movements of the body and/or adapt to its morphology, which can vary greatly between subjects due to sex, age, ethnicity, build and phenotype.

The electrical connectors 14, 15 are configured to transport the signal received by the electrodes to an acquisition and processing device 18 (visible in FIG. 2), arranged on the opposite side to the side at which the detecting surfaces of the electrodes 11 and 12 are foreseen. The acquisition and processing device 18 is an electronic device configured to acquire and process the signals detected by the electrodes and transmitted through the electrical connections 16, 17 to the electrical connectors 14, 15.

Such an acquisition and processing device 18, per se known, is for example a mono- or multi-derivation electrocardiographic device, holter ECG, heart rate monitors, multi-parameter polygraphs or actigraphs, bioimpedance measurers of breathing parameters or for measuring strain gauges that may or may not be textile. Preferably, the device 18 is arranged outside the fabric structure 13. Preferably, the sensor of FIGS. 1-3 is applied to a garment, for example casual, clinical and sports clothing, for adults (men and women), the elderly (men and women), pregnant women and/or children, or to a thoracic belt. When worn, the upper surface of the sensor and therefore the upper surface of the textile structure is placed in direct contact with the skin. Since the detecting portion 11a and 12a of the electrodes is in relief with respect to the remaining portions of the upper surface of the textile structure, the skin comes into contact mainly with such portions with consequent increase in adherence of the active parts of the sensor. Preferably, the textile structure 13 is applied to a garment through a band 19 (only visible in FIG. 1), which is arranged so as to lay over the edge of the textile structure 13, indicated with a dotted line 21 in FIG. 1, and over a portion of a garment (not shown in FIGS. 1-3) directly adjacent to the textile structure so as to glue the structure to the garment. The band is preferably made from polymeric material and can be applied through heat bonding, preferably thermowelding, using conventional thermowelding machines, or pressing using a conventional plate, so as to glue or in any case attach the sensor to the garment. Preferably, the band is formed from a film of polymeric material that is elastic under traction.

Preferably, the polymeric material from which the band is made has an elongation at break greater than or equal to 150%. This allows greater freedom of movement for the user wearing the garment provided with the biomedical and/or biometric sensor, since the sensor is able to extend at least as far as the garment in which it is integrated, if the latter is made from elastic or bi-elastic material or from seamless fabric, like for example typically in garments intended for sports activities.

Such a band can be made up of just the polymeric film or of a polymeric film coupled, through two-sided adhesion, with other materials, which may also be textile, capable of improving its aesthetics and comfort.

In an embodiment, for example for application to sports clothing, the band has a surface width comprised between 0.7 cm and 1.5 cm.

In an embodiment, the textile structure 13 is obtained by frame-weaving conductive threads of fibres of elastomeric polymer coated with metal with (non-conductive) functional threads of fibres of elastomeric polymer. In this way, the textile structure is flexible and elastic in elongation.

The Applicant has studied and experimentally verified that the presence of the band of impermeable material that at least partially surrounds the textile electrode and is adjacent to it increases local sweating, in a region adjacent to the electrical connection region, of the skin of a user with which the electrode comes into contact. An increase in sweating takes place in the area covered by the detecting portion of the textile electrode, in this way reducing the contact resistance between electrode and skin and thus increasing the efficiency of detection of the signals.

In some embodiments, the union of the textile electrode through band application can be advantageous since it keeps the sensor perfectly stuck onto the garment without creating protrusions and keeps the edge of the sensor itself smooth, and therefore comfortable, and it promotes the adherence of the sensor to the epidermis. The artefacts from sliding of the fabric on the skin are reduced thanks to the greater adherence and surface friction without this producing discomfort for anyone wearing the sensor-applied garment.

For example, the band comprises a film of biocompatible polyurethane. Depending on the application, the band can have just one adhesive side (the lower side that glues the textile structure to the garment) or both sides adhesive. In some preferred embodiments in which the band is impermeable to water and not breathable, the film of polyurethane is in direct contact with the skin of whoever wears the sensor.

In an embodiment, the band of polyurethane is coupled with a natural fabric, such as cotton jersey, placed in contact with the skin, for example for continuous use on a child or an elderly person.

Preferably, the outer thickness of the band 19 with respect to the reference plane of the textile structure (plane XY) is less than the external thickness (or height) of the detecting portions of the textile electrodes, again with respect to the reference plane, so that the active portion of each electrode protrudes both with respect to the respective adjacent peripheral portions and with respect to the band 19. In some embodiments, the height of the detecting portions is comprised between 0.1 mm and 10 mm.

The configuration of the electrode, with the conductive portion protruding with respect to the main surface of the textile electrode, together with the presence of a band made from impermeable and non-breathable material in a region close to the active region of the sensor, increases the adherence of the electrode to the skin and at the same time the humidity of the skin, thus further improving the efficiency of detection of biosignals.

In preferred embodiments, the textile structure 13 is a Jacquard fabric. In accordance with the present description, by Jacquard fabric we mean a fabric manufactured with a Jacquard frame and woven thread by thread. The Jacquard frame can be a per se known frame, actuated electronically, for example computer-controlled. The electrodes are woven into a fabric structure (indicated with 13 in FIGS. 1-3) by weaving conductive threads with functional threads in the weaving steps.

The textile structure is formed by the orthogonal crossing of warp threads and weft threads. Generally, the fabric structure is constructed by weaving a first plurality of threads, parallel to one another, which constitute the warp, with a second plurality of threads, parallel to one another, which constitute the weft. In known ways, the weaving between warp and weft takes place, in an electronic Jacquard frame, by unwinding the warp from the beam of the frame, lifting or lowering the warp threads thus creating a "pitch", and inserting a weft inside the pitch, then beaten by a comb. The weft is pulled and pushed from one selvage to the other of the fabric in different ways, such as air jet, water jet, a projectile or a pincer (positive or negative). A fabric can be constructed with more than one weft that intersects the warp. In some embodiments, the fabric of the textile structure is a brocade fabric or a damask fabric.

Preferably, the fabric of the detecting portion of the electrodes intended to come into contact with the skin is a woven fabric that is permeable to water and breathable. Preferably, the textile structure that comprises the electrodes is made from woven fabric, which is permeable and breathable.

Preferably, the textile structure that comprises at least one textile electrode is made in a single weaving operation through a Jacquard frame. The textile structure can thus be formed without stitching, in other words formed from a single fabric element, i.e. in a single piece.

In an embodiment, the textile electrode comprises a fabric the warp of which consists of conductive threads, whereas the weft consists of functional threads, for example cotton or synthetic material, such as polyester. In per se known ways, the detecting textile portion of the textile electrode can be made with an electronic frame having a control unit configured to carry out a weaving programme, which defines the order of the threads and the bindings, weaving the conductive warp threads with the functional weft threads so that, in the layer intended to come into contact with the skin, the conductive threads are left mainly on the surface so as to form an upper surface of electrically conductive fabric.

With reference to FIGS. 1-3, the textile structure has an upper surface that is substantially flat and arranged in the plane XY except in the portions of electrically conductive fabric that form the detecting portions of the electrodes, the surface of which has a finite height with respect to the plane XY. In such an embodiment (FIG. 3), the shape of each textile electrode is approximately bi-convex, i.e. both the upper surface and the lower surface of the textile structure at the electrodes is, approximately, outwardly convex.

The textile electrode 11 and 12 comprises a three-dimensional fabric structure that comprises the conductive detecting fabric portion that forms an upper layer of the structure the surface of which is intended to come into contact with the skin and a lower fabric layer, arranged below the upper fabric layer and joined to the latter along a perimeter joining line so as to create a cavity defined by the joining line. In the present embodiment the joining line substantially corresponds to the outer edge of the detecting portion 11*a* and 12*a*. The region outside the perimeter line comprises the peripheral fabric portion 11*b* and 12*b* adjacent to the detecting portion. Preferably, each peripheral portion extends externally from the respective perimeter joining line. Both the upper and lower layers of the 3D structure are made with a frame and a joined directly in the Jacquard processing along the perimeter joining line so as to create two separate layers of fabric in a region inside the perimeter line that forms a pocket and a "single" fabric at the peripheral portions. The protrusion of the detecting portion is made by inserting a filler material 20 in the cavity. Preferably, the filler material 20 is a polyester fibre, more preferably a continuous filament of microfiber polyester.

Preferably, the filler material is a ball of polymeric fibre, more preferably a ball of microfiber polyester fibre, even more preferably a ball of continuous filament of microfiber polyester.

In some preferred embodiments, which comprises the embodiment of FIGS. 1-3, the textile structure of the sensor is a Jacquard double weave that comprises two three-dimensional textile electrode structures. Each 3D structure comprises a first layer of conductive fabric and a second layer of fabric, in which the first layer of fabric lays over the second layer and joined to it along a joining line so as to form a pocket or, more generally, a cavity defined by the joining line. Preferably, the joining line is a closed perimeter line. In the embodiment of FIGS. 1-3, the 3D fabric structure that forms each electrode is woven into the fabric structure 13. Preferably, the second layer extends, before insertion of the filler material 20, in a plane parallel to the plane on which the first layer lies, over an area corresponding to the area of the detecting portion of the electrode. The second layer, arranged below the first layer, is preferably of conductive fabric.

With the Jacquard technique, tubes or pockets of fabric can be formed by weaving, in sequence, a single-layer fabric, then, along both the warp direction and the weft direction, a double-layer fabric to go back to single-layer weaving. The transition points from single layer to double layer and vice-versa, in the warp and weft directions, correspond to the perimeter joining line of the cavity.

FIG. 4 schematically shows a cross section of the structure of a double fabric, in particular with double warp, for constructing a pocket through a Jacquard frame. In particular, the three-dimensional structure comprises a first warp layer and a second warp layer arranged below the first warp layer and in a plane parallel with respect to the plane in which the first warp layer lies. The first warp layer is made from a first plurality of conductive threads 81, parallel and coplanar to one another, whereas the second warp layer is made from a second plurality of conductive threads 81, parallel and coplanar to one another, preferably arranged so that the threads of the second plurality are arranged one by one at the threads of the first plurality and opposite them. A respective first and second plurality of threads 83 and 86 of base weft (indicated in FIG. 4 with a continuous line) weaves the respective plurality of warp threads 81 and 82 passing over and under each warp thread of the respective first and second warp layer. It should be noted that the base weft threads 83 (86) pass above and below the warp threads 81 (82) forming what is defined as base fabric arranged in a plane corresponding to that of the first (second) warp layer. The base warp and weft threads 81 and 83 and 82 and 84 thus form two base weft-warp layers, upper and lower, parallel to one another. Preferably, the weft threads are functional threads, for example made from polyester or nylon, cotton or chenille.

A first plurality of joining weft threads 84 (indicated in the figures with a dotted and dashed line) interweaves at least one sub-plurality of the first plurality of warp threads 81, i.e. in the plane of the first warp layer (or of the upper base fabric), and joins the first warp layer with the second warp layer weaving at least one first and a second warp thread 82 of the second warp layer spaced apart in the direction perpendicular (axis X) to the direction of the warp threads (axis Z). In this way, at the points in which the first plurality of joining weft threads 84 interweaves the second warp layer, the first warp layer is joined to the second warp layer along the axis Z of the thickness of the fabric. Preferably, the first plurality of weft threads interweaves the second warp layer 82 in a first sub-plurality of mutually adjacent warp threads 82 that defines a first joining region 90 and in a second sub-plurality of mutually adjacent warp threads 82 that defines a second joining region 89, the first and the second joining region being spaced apart along the direction of the weft. For the sake of clarity, in FIG. 4 the warp threads of the first and second plurality of threads 81 and 82 are shown still separate from one another in the joining regions 89 and 90.

The inner region between the two joining regions 89 and 90, at which a weft thread interweaves both the warp threads of one layer and at least two warp threads, spaced apart from one another, of the other warp layer, forms an open double layer region, having an upper fabric layer and a lower fabric layer, separated from one another; such a region will be indicated as cavity. In the example of FIG. 4, the open region is an open warp double fabric. The cavity can be filled by a filler material so as to create a cushion-effect in the fabric portion corresponding to the cavity. Preferably, the first and second warp layer are also joined in the direction of the weft along two joining lines, parallel to one another and spaced apart from each other in the direction of the warp. In this way, the first and the second warp layer are joined along four sides, e.g. in the warp and weft directions, by a closed joining perimeter line that defines a cavity. The surface of the upper fabric layer in the region inside the joining regions 89 and 90 is electrically conductive since it forms the detecting area of the sensor. For this purpose and in accordance with an embodiment, the warp threads 81 (82) and the base weft thread 83 (86) of the 3D structure of each electrode are electrically conductive.

The joining regions 89 and 90 have a finite width and preferably extend along a plurality of warp threads of the upper layer and of the lower layer. In the joining regions the double fabric has the two juxtaposed warp layers constructed in a single in a single fabric layer, i.e. closed warp double fabric. The fabric architecture exemplified in FIG. 4 is a multi-layer 3D fabric obtained by interlacing two 2D weft-warp fabrics with an additional series of threads that act as joining threads in the direction of the thickness of the fabric (axis Z in the figures), in which the majority of weft threads is arranged in the plane of the respective warp layer and only selected threads (i.e. the joining threads) are used to join the two warp layers together.

The example described above is a double fabric construction with two warps and three wefts, one weft of which is the joining weft. Optionally, a first plurality of brocade threads 85 is interweaved with at least one sub-plurality of threads 81 of the first plurality of warp threads. A second plurality of brocade weft threads 88 is interweaved with at least one sub-plurality of threads 82 of the second plurality of warp threads. The first and the second plurality of brocade threads 85 and 88 are indicated in the figures with a broken line. In some embodiments, a second plurality of joining weft threads 87 interweaves a sub-plurality of the second plurality of warp threads 81, i.e. in the plane of the second warp layer, and at least one first and a second warp thread 81 of the first warp layer, in which the first and the second warp thread of the first layer are spaced apart in the direction of the weft.

Figure 5:
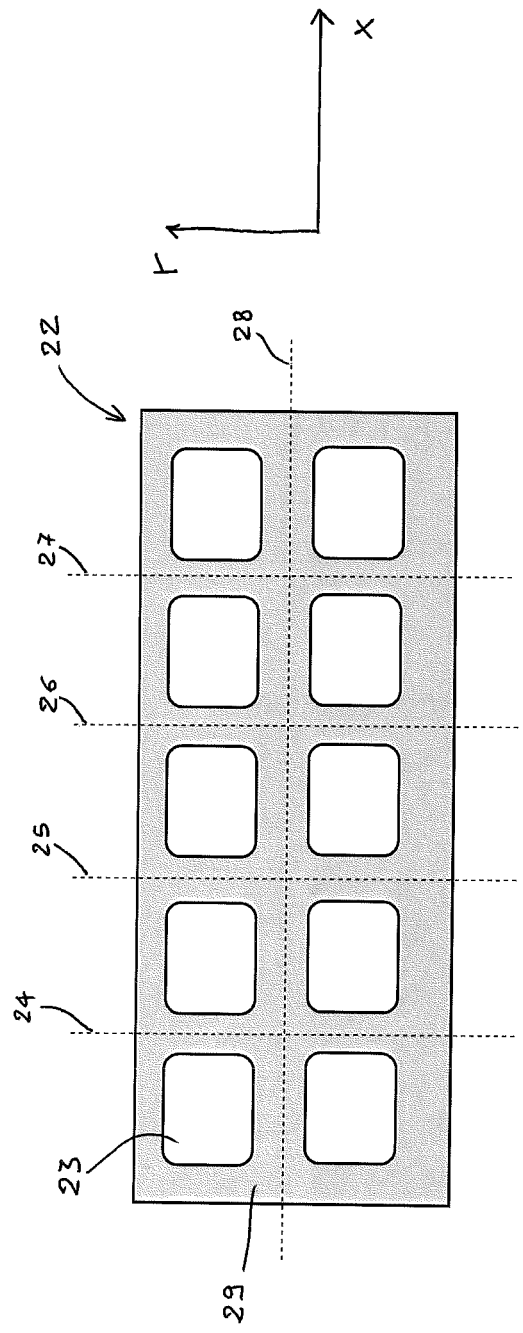
FIG. 5 shows a textile structure from which it is possible to obtain a plurality of textile electrodes according to an embodiment of the invention.

FIG. 5 exemplifies a way to make a plurality of 3D electrode structures, each containing a cavity defined by a closed joining line. A textile structure 22, shown in a front view in plan, is made in a single piece by means of a Jacquard frame. The direction Y indicates the warp direction, whereas the direction X indicates the weft direction. The textile structure 22 is a double fabric with double warp structure, which comprises a plurality of fabric regions 23 (indicated with the colour white), at which the fabric is an open warp fabric made up of an upper fabric layer and a lower fabric layer separated from one another. The regions 23 are spaced apart by peripheral regions 29, which surround each region 23, the peripheral regions being of closed warp double fabric (i.e. single layer of fabric), indicated in FIG. 5 with the colour grey. With reference to the example of FIG. 4, the peripheral regions 29 that space apart the regions 23 along the direction X of the weft are the regions of fabric 89 and 90, in which at least one weft thread joins the upper layer to the lower layer of warp and forms a closed fabric. The regions 29 that separate the regions 23 from one another along the directions X and Y are obtained by applying a closed warp double weave, i.e. with a single layer of fabric. The upper surface of the regions 23 is electrically conductive and is formed by bringing conductive weft threads and/or conductive warp threads to the surface.

After the fabric structure 22 has been completed, the structure is cut along the vertical lines 24-27 and the horizontal line 28 to obtain a plurality of electrodes, each formed by a region 23 and a portion of peripheral region 29 that surrounds the region 23. The cutting of the structure 22 can be carried out using per se known machines for laser or ultrasound cutting of fabrics for producing textile labels.

The number of weft threads shown in FIG. 4 is purely an example. For example, it should be understood that a plurality of weft threads can bind the first warp layer to the second warp layer and/or the number of weft threads that form the 2D fabric on the two warp layers can be different from that shown in FIG. 4.

It should be understood that the weaving process can be controlled so that the structure 22 is made by exchanging weft and warp, i.e. it is a double weft structure with 3D portions in which two weft layers are open and joining regions in which the wefts are closed.

It should be understood that the 3D structure that constitutes the electrode can be formed from conductive weft threads and functional warp threads, alternating functional threads and conductive threads both in weft and in warp, or using conductive threads both in weft and in warp in the electrically conductive portion of the electrode, e.g. the detecting portion.

The cavity formed at the open region with its separate fabric layers can be shaped like a pocket, like in FIGS. 1-3, or it can be tubular shaped. The filler material is preferably a hydrophilic ball of polymeric fibre, which is able to absorb the humidity that passes through the fabric of the electrode and is caused by the sweat or perspiration of the body with which the electrode is in contact. The ball forms a padding that in this way acts as a "reservoir" of the electrode, since it holds the water, sweat or an aqueous solution, applied by the user (for example during a sports activity), or a water-based gel typically used for ECG measurements, releasing it gradually improving the transmission of the signal over time. Preferably, the filler material is a ball of polyester fibre, preferably a ball of continuous filament of microfiber polyester.

Figure 6:
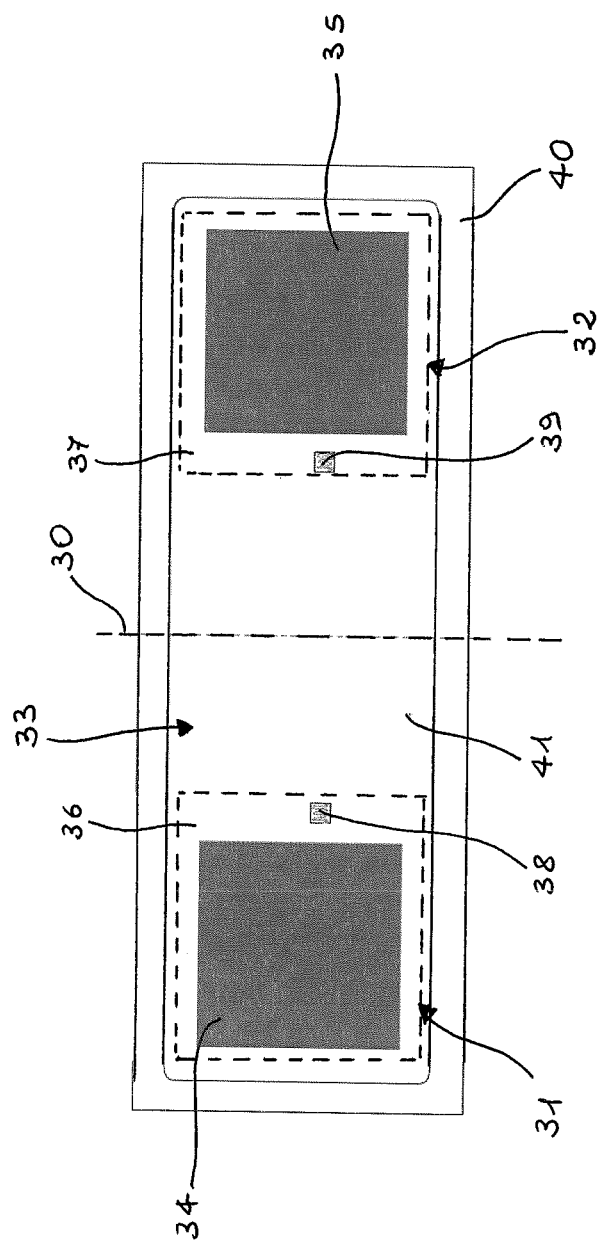
FIG. 6 is a front view from above of a biomedical and/or biometric sensor according to a further embodiment.

In the embodiment of FIGS. 1-3, the electrical connection 16, 17 is a metallic thread or a conductive textile string fixed, at its ends, on the electrode 11, 12 and on the connector 14, 15. In some embodiments, the electrical connection between the detecting portion of the electrode and the connector is woven into the textile structure 13. FIG. 6 shows a biomedical and/or biometric sensor in accordance with a further embodiment. The sensor comprises a first textile electrode 31 and a second textile electrode 32. The first and the second electrode are integrated in a textile structure 33, preferably a textile label made with a frame, preferably a Jacquard frame. Each textile electrode comprises a respective detecting portion 34, 35 and a respective peripheral portion 36, 37 that in the figures is illustrated as being an area defined by a broken line. The peripheral portion is directly adjacent to and surrounds the respective detecting portion.

Each textile electrode 31, 32 is made from fabric by interweaving electrically conductive threads with functional threads (non-electrically conductive) so that the conductive threads are arranged on the upper surface of the detecting portion 34, 35 that extends over a detecting surface area (i.e. exposed on the surface for contact with the skin), while they remain enclosed inside the fabric at a peripheral surface area of the peripheral portion 36, 37. In the peripheral surface area, the functional threads are arranged on the upper surface that therefore is not electrically conductive, while the conductive threads are arranged in the inner part of the fabric. In this embodiment, the conductive threads are therefore alternatively exposed to the outside or enclosed inside the fabric. Preferably, the detecting portion 34, 35 of each electrode protrudes in height outwards with respect to the peripheral portion.

In each peripheral portion, the conductive threads inside the structure in the peripheral surface area are brought to the outside, on the upper surface, in a textile connection region 38, 39 that is arranged, on the upper surface of the sensor, spaced, i.e. not in contact, from the respective detecting portion, being separate from the peripheral surface area. Each contact region can have an electrical connector (not shown in the figures), for example of the snap-on type applied to it, so as to carry the signals detected by the electrode to an acquisition and processing device of electrical signals (not shown). The acquisition and processing device of signals can be arranged adjacent to and separate from the textile structure or on the back of it. The electrical connection between the detecting portion 34 of the electrode 31 and the respective connection region 38 is made by the conductive thread woven inside the fabric of the peripheral region 36 of the electrode. The electrical connection between the detecting portion 35 of the electrode 32 and the respective connection region 39 is made by the conductive thread woven inside the fabric of the peripheral region 37 of the electrode.

In the electrode, the conductive threads are arranged by the frame-processing so that they are alternately exposed to contact with the skin and in any case with the outside or enclosed inside the fabric itself. This means that in some points defined as "contact points" the conductive part is available to act with external elements like for example the skin or the connectors, and in other areas the conductive part remaining inside has the function of transmitting the signal between the various contact parts.

According to an embodiment, in FIG. 6, the textile structure of each electrode is made in warp with conductive thread. In some regions of the electrode, corresponding to the detecting portion and to the connection region (for the attachment of the snap-on connector), the conductive warp thread emerges, whereas in the region of the peripheral portion different from the connection region, the conductive warp thread remains inside and transmits the signal from the detecting portion to the snap-on connector. Preferably, the region 41 of the textile structure 33, different from the region corresponding to the electrodes 31 and 32 is entirely made with functional threads, not conductive, both in weft and in warp, to avoid electrical contact between the two electrodes 31 and 32. Optionally, the textile structure 33 is applied to a garment (not shown in the figures) through a thermoadhesive polymeric tape 40 that fixes the edge of the textile structure to the garment and is preferably impermeable.

Preferably, the textile electrodes and in general the textile structure that comprises one or more electrodes is made from Jacquard fabric. For example, the electrically conductive surface of the detecting portion of the electrode is obtained by weaving an additional brocade weft made of conductive threads that cross over a warp of conductive or functional threads, such an additional weft being in relief with respect to a base weft formed from functional threads that cross over the warp.

Each electrode 31, 32 has a 3D textile structure, in which the detecting portion 34, 35 comprises two electrically conductive fabric layers, juxtaposed and connected to one another: an upper textile layer the outer surface of which (visible in FIG. 6) that is intended to come into contact with the skin of the individual and a lower textile layer. The upper and lower layers are joined together directly in the Jacquard processing along a perimeter joining line so as to create a cavity, subsequently filled with a filler material so as to make the detecting portion of each electrode protrude in height with respect to the remaining portions of the sensor, i.e. portions 36, 37, and preferably the portion 41. In an embodiment, the lower layer can be made from functional fabric, i.e. not electrically conductive.

It should be understood that, depending on the application and therefore on which physiological electric signals are wished to be measured, the textile structure 33 can comprise a single textile electrode or more than two textile electrodes.

Figure 7:
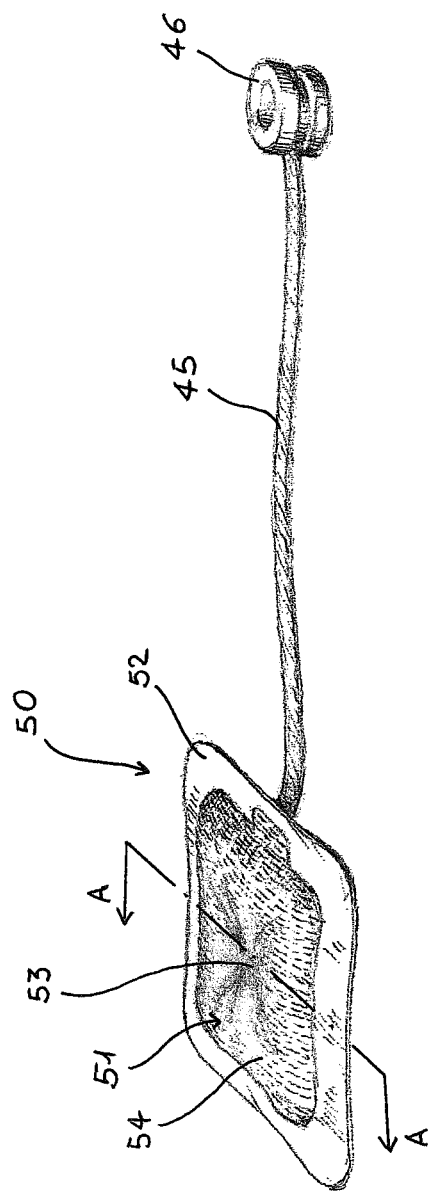
FIG. 7 shows a sensor for measuring physiological electric signals according to a further embodiment of the invention.

FIG. 7 schematically shows a sensor for measuring physiological electric signals in accordance with an embodiment of the invention. The sensor comprises a textile electrode 50 that comprises a detecting portion 51, the upper surface of which is of electrically conductive fabric and extends over a detecting surface area, and a peripheral textile portion 52 that surrounds and is directly adjacent to the detecting portion. The detecting portion 51 protrudes outwards with respect to the peripheral portion 52 so as to have a finite thickness in height with respect to the peripheral portion. An electrically conductive textile string 45 electrically connects the textile electrode 50 to a snap-on connector 46. The electronics for measuring and processing the signals, which is electrically connected to the connector 46, is not shown in the figures. In some embodiments, the use of a conductive textile string is useful for detecting and transporting the signal in different points of the garment in which it is integrated and without having to submit to the weaving "directions" of the garment itself since the string can be arranged horizontally, longitudinally or transversally with respect to the weaving of the garment.

The textile connection string can be joined to the garment by taping, sewn, embroidered, or inserted in a textile sheath in turn sewn onto the garment itself. Preferably, the electrically conductive textile string is elastic in elongation and preferably also in torsion and/or flexing, so as to follow the movements of the garment on the body, in this way ensuring comfort and ease of use, for example during sports activities. The textile string 45 is preferably a bundle of woven threads, which comprises electrically conductive threads of elastomeric polymer fibres coated in metal.

Preferably, the detecting fabric portion 51 of the electrode protrudes outwards by a variable height comprising at least one recess 53. The electrode of FIG. 7 comprises a single recess 53, arranged centrally with respect to the detecting portion 51. For example, in the transversal section of the thickness of the textile electrode, the portion 51 has a convex or concave shaped outer surface, towards the outside of the electrode.

Figure 7B:
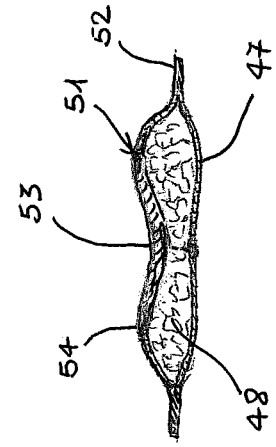
FIG. 7b is a cross section of FIG. 7 along the line AA.
Figure 7A:
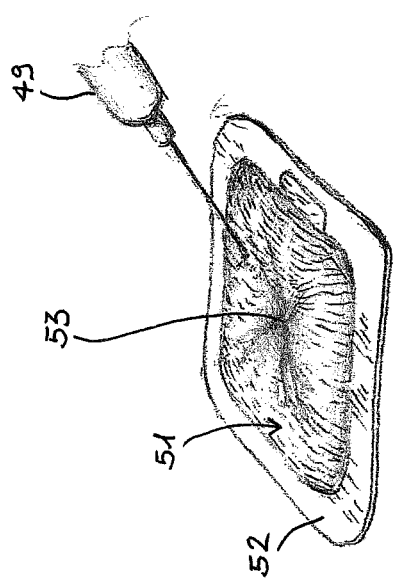
FIG. 7a shows a detail of FIG. 7, which refers to the injection of the filler material.

FIG. 7a shows a detail of FIG. 7, whereas FIG. 7b is a cross section of FIG. 7 along the line AA that passes through the recess 53.

Preferably, the textile electrode 50 is manufactured in Jacquard fabric as a single fabric element of unitary construction. During the weaving process an inner pocket is formed in the structure of the electrode, of open warp double fabric, defined by a perimeter transition line to a closed warp double fabric. With reference to the embodiment of FIGS. 7, 7a-7b, the recess 53 can be formed by joining the two upper and lower warp layers in a further intermediate point between the points that form the perimeter line of the cavity. It should be noted that the Jacquard weave makes it possible to create complex padding patterns, for example with a distribution of convexity and concavity on the surface of the detecting portion, through a single weaving process.

In particular, the electrode 50 is constructed in double Jacquard fabric that comprises a detecting portion having an open warp double layer textile structure that comprises an electrically conductive upper fabric layer 51 that constitutes the detecting surface of the electrode, in which the upper fabric layer lays over a support fabric layer 47 arranged below and opposite the layer 51. The upper and lower fabric layers are joined together along a perimeter joining line that defines the detecting portion so as to leave the two layers separate and juxtaposed in a region inside the perimeter line, such an inner region forming a cavity. The double fabric is made with closed warps in the peripheral portion 52 of the electrode, in which the warps are woven in a single layer. Preferably, the fabric layer at the peripheral portion is not electrically conductive, for example it is constructed with functional threads in warp and weft.

The cavity is filled by a filler material 48, which creates the height of the protrusion of the detecting portion 51. The filler material 48 is preferably inserted in the completed textile electrode, through insertion of polymeric material with fibre that expands, after insertion, or more generally that creates a ball of thread. The ball can have dimensions that are variable and selectable at the production stage and as a function of the target user, the application and the context where the measurement and/or monitoring is carried out.

In some embodiments, the filler material is a continuous filament of microfiber polyester. It is strong, by nature holds its shape well, and once "injected" it swells by its nature creating a soft ball. The ball of filament of microfiber polyester has the advantage of being crease-resistant, absorbing sweat/water, i.e. of being hydrophilic, without becoming impregnated and therefore acting as a slow-release water reservoir. Once the ball of thread is wet it does not deform and when drying easily foes back to the original non-swollen shape. In the embodiment of FIG. 7, a continuous filament is pressure-injected, for example using compressed air, through a needle 49 inserted in the fabric of the detecting portion of the electrode.

Figure 8:
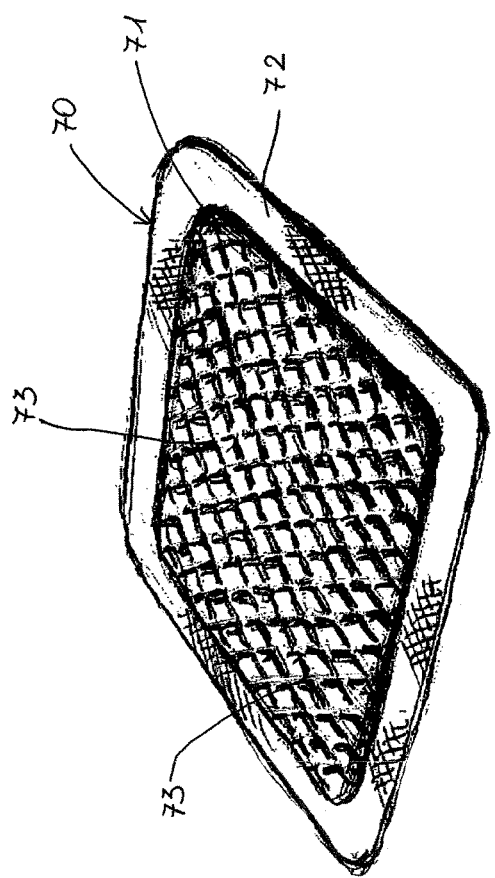
FIG. 8 shows a textile electrode for a sensor for measuring physiological electric signals according to another embodiment.

Other embodiments foresee a plurality of recesses inside the conductive portion of the electrode. FIG. 8 shows a textile electrode 70 that comprises a detecting portion 71 and a peripheral portion 72 that surrounds the detecting portion. The detecting portion protrudes outwards in height with respect to the peripheral portion and comprises a plurality of recesses 73 that create local variations in height that, in some embodiments, increase the adherence of the electrode to the skin of whoever wears it and thus greater efficiency of detection of the signal. As an example, the plurality of recesses is arranged in an organised arrangement that covers the entire surface of the detecting portion. The textile corresponding to the detecting portion is padded with a filler material that creates the protrusion of the detecting portion.

Figure 9:
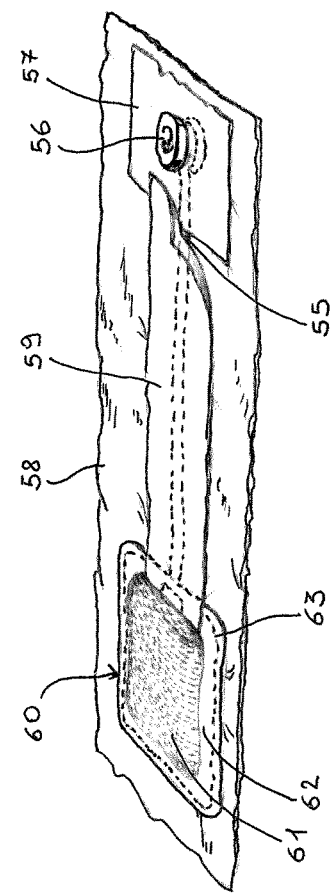
FIG. 9 is a view from above of a sensor according to another embodiment of the present invention.

FIG. 9 shows a biomedical sensor applied to a garment, in accordance with an embodiment of the present invention. A textile electrode 60 comprises a detecting portion 61 and a peripheral portion 62 that surrounds and is directly adjacent to the portion 61. The portion 52 protrudes in height outwards with respect to the peripheral portion. The peripheral portion is sewn onto a garment 58, only a part of which is shown in FIG. 8, along a perimeter sewing line 63. An electrically conductive textile string 55 electrically connects the textile electrode 60 to a snap-on connector 56, in turn connected or connectable to an acquisition and processing device of biosignals, preferably arranged on the side of the garment opposite that of the conductive surface of the electrode and not shown in the figures. The textile connection string 55 is fixed to the garment through a thermoadhesive tape 59, which is arranged above the textile string, along its length. In other embodiments (not shown in the figures), the textile string can be sewn onto the garment or woven directly into the garment creating in the garment a band of electrically conductive fabric, on which it is possible to fix, through taping or sewing, a textile electrode. A reinforcing fabric 57 of the garment 58 can be foreseen at the snap-on connector 56.

Figure 10:
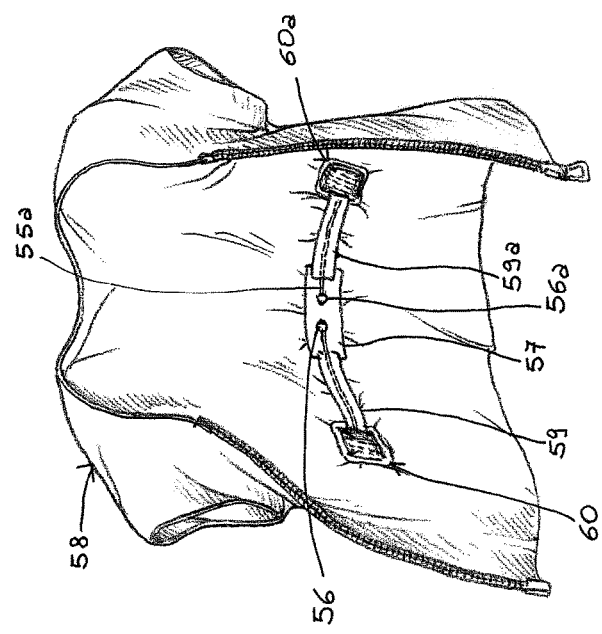
FIG. 10 shows a garment in which a biomedical and/or biometric sensor is applied.

Preferably, the textile string 55 is a cord that is elastic in elongation, flexing and/or torsion, for example a bundle of elastomeric synthetic fibres, such as elastomer polyurethane fibres known by the trade name elastam, or polyester-elastam fibres, coated with conductive material, for example silver. Preferably, the tape 59 is made from polymeric material having elongation at break that is greater than or equal to 150%, so as to follow the movements and the deformations of the body in accordance with the elasticity of the garment. In the embodiment of FIG. 10, the garment 58 is a t-shirt, to which, in addition to a first textile structure described with reference to FIG. 9 (the same reference numerals indicate elements that are the same or that have functionalities similar to those of FIG. 9), a second and substantially identical textile structure is applied, arranged so as to mirror the first textile structure. In particular, the second textile structure comprises a second textile electrode 60a, an electrically conductive textile string 55a, at least partially coated by a thermoadhesive tape 59a that fixes it to the garment 58. The cord 55a connects the textile electrode 60a to a connector 56a. The connectors 56 and 56a are electrically connected or connectable to the same acquisition and processing device of biosignals, which could be arranged on the back of the reinforcement fabric 57 and therefore not visible in the figures.

In an embodiment, the tape is made from silicone and fixes the sensor to the garment through silicone rubber casting.

It should be understood that the position of the sensor in the garment of FIG. 10 is purely for indicating purposes and depends mainly on the electrical signals that it is wished to measure and on the user of the sensor. For example, the sensor of FIG. 10 can be used to record an ECG trace in an adult. In this case, the sensor can be positioned on the garment so that, once the garment is worn, it is in contact with the skin at the thorax of the individual, typically at the height of the sternum. In the case in which the user is a new-born baby or a child, the sensor can be attached to a sleeve of the garment. Again as an example, in the case in which the sensor of FIG. 10 is used to measure breathing, the position of the sensor on the garment can be such that, once worn, the electrodes are arranged on the thorax or on the abdomen area of the individual.

In some embodiments of the present invention, the sensor for measuring physiological electric signals is configured to acquire and process a plurality of biosignals, for example breathing and biological signals, such as ECG, EEG and EMG, for example a configuration of ECG sensors that allows many electrocardiographic derivations to be measured simultaneously.

In some embodiments, the connection portions and the electrode are also made by weaving conductive threads with elastic functional threads, thus obtaining a textile sensor structure with elastic properties, particularly suitable for being applied to sports clothing. Such a textile sensor structure can be sew onto a garment through sewing or applied adhesively to the garment through an elastic polymeric tape.

The invention claimed is:

1. A sensor for measuring physiological electric signals from a skin of an individual, comprising:
   a first textile electrode that comprises a detecting textile portion for detecting physiological electric signals and a peripheral textile portion directly adjacent to the detecting textile portion, the detecting textile portion having an electrically conductive detecting surface area intended to come into contact with the skin of an individual, and
   a first electrical connection configured to electrically connect the first textile electrode to a first electrical connector, the first electrical connection being electrically conductive and elastic textile string;
   the first electrical connector electrically connected to the first textile electrode through the first electrical connection, wherein the first electrical connector is electrically connected to an acquisition and processing device of the physiological signals detected by the first textile electrode,
   the first textile electrode has a three-dimensional textile structure made by weaving together warp threads and weft threads, in which the detecting textile portion comprises an upper textile layer, having an upper surface which extends over the detecting surface area, and a lower textile layer, arranged below the upper textile layer and joined to it along a perimeter joining line so as to create a cavity defined by the perimeter joining line and define a region outside of the perimeter joining line that comprises the peripheral textile portion, and
   the cavity is filled by a filler material so that the detecting textile portion protrudes in height with respect to the peripheral textile portion;
   wherein
   the textile string of the first electrical connection is a bundle of conductive threads made up of fibres of polymeric material having high elastic elongation at break and coated with a conductive layer.

2. Sensor according to claim 1, wherein the peripheral textile portion extends externally from the perimeter joining line and the textile structure of the first textile electrode is a double fabric, in which the detecting textile portion is formed from two separate textile layers corresponding to the upper textile layer and to the lower textile layer, and the peripheral textile portion is interwoven in a single layer.

3. Sensor according to claim 1, wherein the peripheral textile portion comprises a non-electrically conductive peripheral surface area, arranged adjacent to and in contact with the detecting surface area.

4. Sensor according to claim 1, wherein the warp threads and/or the weft threads are elastic.

5. Sensor according to claim 1, in which the textile structure of the first textile electrode is a double warp Jacquard fabric, in which the detecting textile portion is an open warps fabric made up of the upper textile layer and of the lower textile layer, separate from one another, and the peripheral textile portion is a closed warps fabric interwoven in a single layer.

6. Sensor according to claim 1, wherein the first textile electrode is manufactured in Jacquard fabric in a single piece.

7. Sensor according to claim 1, wherein the first textile electrode is made from fabric by interweaving electrically conductive threads with functional threads so that such conductive threads are arranged on the detecting surface area of the detecting textile portion exposed to contact with the skin of the individual wearing the sensor, whereas the conductive threads remain bordered by a non-electrically conductive peripheral surface area comprised in the peripheral textile portion and directly adjacent to the detecting surface area, and wherein the functional threads are exposed on the detecting surface area whereas the conductive threads remain enclosed inside the fabric at the same detecting surface area.

8. Sensor according to claim 7, wherein the functional threads and/or the conductive threads are elastic threads comprising an elastomeric polymer fibre.

9. Sensor according to claim 7, wherein:
   the peripheral textile portion comprises a textile connection region having an electrically conductive surface connection area, arranged adjacent to and outside the non-electrically conductive peripheral surface area, the conductive threads being exposed on the surface connection area, and
   the first electrical connection is made from the conductive threads enclosed inside the fabric of the peripheral textile portion and that extend from the surface detecting area to the connection region.

10. Sensor according to claim 1, which further comprises a sensor textile structure interwoven in a single piece by interweaving electrically conductive threads with functional threads, in which the first textile electrode is integrated, the textile sensor structure comprising a second textile electrode arranged outside the peripheral textile portion of the first textile electrode and a second electrical connection configured to electrically connect the second textile electrode with a second electrical connector, the first and the second electrical connector being electrically connected, respectively, to the first textile electrode and to the second textile electrode through the respective first and second electrical connections, in which the first and the second electrical connector are electrically connected to the acquisition and processing device of the physiological signals detected by the first textile electrode and by the second textile electrode.

11. Sensor according to claim 1, wherein the filler material is a polymeric fibre.

12. Sensor according to claim 11, wherein the filler material is a hydrophilic ball of polymeric fibre.

13. Sensor according to claim 1, wherein a second electrical connection is an electrically conductive and elastic textile string, the textile string of the second electrical connection is a bundle of conductive threads made up of fibres of polymeric material having high elastic elongation at break and coated with a conductive layer.

14. Sensor according to claim 13, wherein the textile string of the first electrical connection is a bundle of interwoven textile threads that comprises electrically conductive threads, wherein the conductive threads are elastic and/or the bundle also comprises elastic functional threads.

15. Sensor according to claim 14, wherein the textile string of the first electrical connection is a bundle of interwoven textile threads of elastomeric polymer coated with a metallic coating.

16. Sensor according to claim 1, wherein the detecting textile portion protrudes outwards by a variable height comprising at least one recess extending inwardly.

17. Sensor according to claim 1, wherein the textile structure of the first electrode is a double fabric, in which the detecting textile portion is formed from two separate textile layers corresponding to the upper textile layer and to the lower textile layer, and the peripheral textile portion is interwoven in a single layer, in which the surface detecting area comprises a recess so that the detecting textile portion protrudes outwards by a variable height, the recess being formed by joining the upper textile layer to the lower textile layer through weaving at a point inside the detecting surface area.

18. A wearable garment to monitor the physiological electric signals of an individual wearing such a garment, such a garment comprising the sensor for measuring physiological electric signals according to claim 1, wherein:

the sensor further comprises a textile sensor structure that comprises the first textile electrode, the textile sensor structure having an outer edge that is peripheral with respect to the first textile electrode and a surface detecting area, the sensor is fixed to the garment with the surface detecting area facing towards the individual through a band that at least partially surrounds the textile sensor structure and that lays over the outer edge of the textile sensor structure and over a portion of the garment directly adjacent to the textile sensor structure so as to fix the textile sensor structure to the garment, and the band is made from polymeric material that is impermeable to water and not breathable.

19. Garment according to claim 18, wherein the band is made from elastomeric polymeric material.

20. Sensor for measuring physiological electric signals from a skin of an individual, comprising:

a first textile electrode that comprises a detecting textile portion for detecting physiological electric signals and a peripheral textile portion directly adjacent to the detecting textile portion, the detecting textile portion having an electrically conductive detecting surface area intended to come into contact with the skin of an individual, and a first electrical connection configured to electrically connect the first textile electrode to a first electrical connector, the first electrical connection being electrically conductive and elastic textile string;

the first electrical connector electrically connected to the first textile electrode through the first electrical connection, wherein the first electrical connector is electrically connected to an acquisition and processing device of the physiological signals detected by the first textile electrode, the first textile electrode has a three-dimensional textile structure made by weaving together warp threads and weft threads, in which the detecting textile portion comprises an upper textile layer, having an upper surface which extends over the detecting surface area, and a lower textile layer, arranged below the upper textile layer and joined to it along a perimeter joining line so as to create a cavity defined by the perimeter joining line and define a region outside of the perimeter joining line that comprises the peripheral textile portion, and the cavity is filled by a filler material so that the detecting textile portion protrudes in height with respect to the peripheral textile portion;

wherein:

the detecting surface area comprises a plurality of recesses so that the detecting textile portion protrudes outwards by a variable height, the recesses defining local variation in height of the detecting surface area.

* * * * *